(12) United States Patent
Gottschling et al.

(10) Patent No.: US 9,029,360 B2
(45) Date of Patent: May 12, 2015

(54) PYRAZOLOPYRIMIDINES AS METABOTROPIC GLUTAMATE 5 RECEPTOR ANTAGONISTS

(71) Applicants: Dirk Gottschling, Mittelbiberach (DE); Heiner Ebel, Biberach an der Riss (DE); Doris Riether, Biberach an der Riss (DE); Bernd Wellenzohn, Friedrichshafen (DE)

(72) Inventors: Dirk Gottschling, Mittelbiberach (DE); Heiner Ebel, Biberach an der Riss (DE); Doris Riether, Biberach an der Riss (DE); Bernd Wellenzohn, Friedrichshafen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 94 days.

(21) Appl. No.: 13/851,189

(22) Filed: Mar. 27, 2013

(65) Prior Publication Data

US 2013/0261105 A1    Oct. 3, 2013

(30) Foreign Application Priority Data

Mar. 29, 2012  (EP) .................................. 12162088

(51) Int. Cl.
| | | |
|---|---|---|
| *A61K 31/55* | (2006.01) | |
| *C07D 487/04* | (2006.01) | |
| *C07D 487/12* | (2006.01) | |
| *C07D 513/04* | (2006.01) | |
| *C07D 495/04* | (2006.01) | |
| *C07D 471/04* | (2006.01) | |

(52) U.S. Cl.
CPC ............ *C07D 513/04* (2013.01); *C07D 487/04* (2013.01); *C07D 495/04* (2013.01); *C07D 471/04* (2013.01)

(58) Field of Classification Search
CPC ..... A61K 31/55; C07D 487/04; C07D 487/12
USPC .......................... 514/215; 540/578, 580, 593
See application file for complete search history.

(56) References Cited

FOREIGN PATENT DOCUMENTS

| WO | 2004089471 A2 | 10/2004 |
|---|---|---|
| WO | 2011015343 A1 | 2/2011 |

OTHER PUBLICATIONS

Bermundo-Soriano, Carlos Riaza et al. "New Perspectives in Glutamate and Anxiety" Parmacology, Biochemistry and Behavior (2012) pp. 752-774.
Friedmann, Claude T.H. et al. "Phase II Double-Blind Controlled Study of a New Anxiolytic, Fenobam (McN-3377) vs Placebo" Current Therapeutic Research, (1980) vol. 27, No. 2, pp. 144-151.
International Search Report for PCT/EP2013/056455 mailed May 21, 2013.
Lindemann, Lothar et al. "CTEP: A Novel, Potent, Long-Acting, and Orally Bioavailable Metabotropic Glutamate Receptor 5 Inhibitor" The Journal of Pharmacology and Experimental Therapeutics (2011) vol. 339, No. 2, pp. 474-486.
Maeng, Sungho et al. "The Role of Glutamate in Mood Disorders: Results from the Ketamine in Major Depression Study and the Presumed Cellular Mechanism Underlying its Antidepressant Effects" Current Psychiatry Reports (2007) vol. 9, pp. 467-474.
Pecknold, John C. et al. "Treatment of Anxiety Using Fenobam (a Nonbenzodiazepine) in a Double-Blind Standard (Diazepam) Placebo-Controlled Study" Journal of Clinical Psychopharm., (1982) vol. 2, No. 2, pp. 129-133.
Porter, Richard H.P. et al. "Fenobam: A Clinically Validated Nonbenzodiazepine Anxiolytic is a Potent, Selective, and Noncompetitive mGlu5 Receptor Antagonist with Inverse Agonist Activity" The Journal of Pharmacology and Experimental Therapeutics (2005) vol. 315, No. 2, pp. 711-721.
Silverman, Jill L. et al. "Negative Allosteric Modulation of the mGluR5 Receptor Reduces Repetitive Behaviors and Rescues Social Deficits in Mouse Models of Autism" Science Translational Medicine (2012) vol. 4, Issue 131, 131ra51, pp. 1-9.

*Primary Examiner* — Brenda Coleman
(74) *Attorney, Agent, or Firm* — Michael P. Morris; Usha R. Patel

(57) ABSTRACT

This invention relates to novel pyrazolopyrimidines and their use as metabotropic glutamate 5 receptor antagonists (mGlu5 receptor antagonists), pharmaceutical compositions containing the same, and methods of using the same as agents for treatment or amelioration of mGlu5 receptor mediated disorders.

5 Claims, No Drawings

PYRAZOLOPYRIMIDINES AS METABOTROPIC GLUTAMATE 5 RECEPTOR ANTAGONISTS

FIELD OF THE INVENTION

This invention relates to novel pyrazolopyrimidines and their use as metabotropic glutamate 5 receptor antagonists (mGlu5 receptor antagonists), pharmaceutical compositions containing the same, and methods of using the same as agents for treatment or amelioration of mGlu5 receptor mediated disorders.

BACKGROUND OF THE INVENTION

The physiological role of metabotropic glutamate receptors is to control and regulate the presynaptic release and the postsynaptic effects of glutamate. Metabotropic glutamate 5 receptors (mGlu5 receptors) are primarily localized to the periphery of the post-synaptic densities of asymmetrical synapses (R. Lujan et al., Europ. J. Neurosci. (1996), 8, 1488-1500), where they function to enhance cellular excitability via interactions with ionotropic glutamate receptors and other postsynaptic processes. Because of their subcellular localization at the periphery of synapses, mGlu5 receptors further boost active synapses, whereas they remain mainly inactive during basal glutamatergic transmission. For this reason, mGlu5 receptor antagonists are hypothesized to be effective in states of glutamatergic hyperactivity whereas their effect on glutamatergic transmission under basal conditions is limited. On the other hand, mGlu5 agonists are effective in states of glutamatergic hypoactivity. mGlu5 receptor activation increases intracellular $Ca^{2+}$ concentration by potentiation of NMDA currents and $Ca^{2+}$ release from intracellular pools. Elevated intracellular $Ca^{2+}$ levels determine the expression of NMDA receptor-dependent long-term potentiation (LTP) and long-term depression (LTD) and hippocampal synaptic plasticity (Bikbaev et al., PlosOne (2008) 3, 2155). Expression of mGlu5 has been seen mainly in the cortex, hippocampus, subiculum, olfactory tubercle, striatum and nucleus accumbens (F. Ferraguti & R. Shigemoto, Cell Tisue Res (2006) 326, 483-504), which suggests an important contribution of mGlu5 receptors to cognitive and basal ganglia related functions. Based on the expression pattern of mGlu5 receptors and their biological function, mGlu5 antagonists have therapeutic potential for the treatment of diseases involving glutamatergic hyperactivity including anxiety, depression, pain addiction, gastro-esophagial reflux disease (GERD) Parkinson's disease, epilepsy, cancer, overactive bladder, aggression, fragile X or autism (Jaeschke et al., Expert Opin. Ther. Patents (2008) 18, 123-142). Several types of antagonists of the mGlu5 receptor have already been described in the literature.

WO2004/089471 discloses pyrazolopyrimidines which are claimed to act as antagonists of the activity of 11β-hydroxysteroid dehydrogenase type 1 (11βHSD1).

DETAILED DESCRIPTION OF THE INVENTION

The present invention provides novel pyrazolopyrimidines, namely

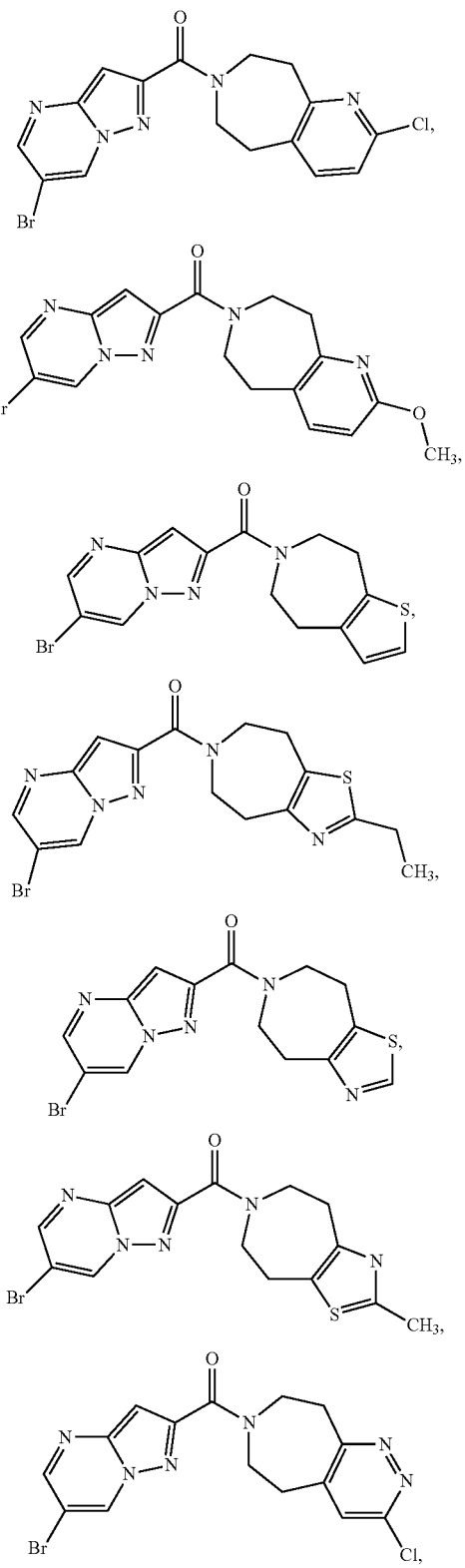

-continued

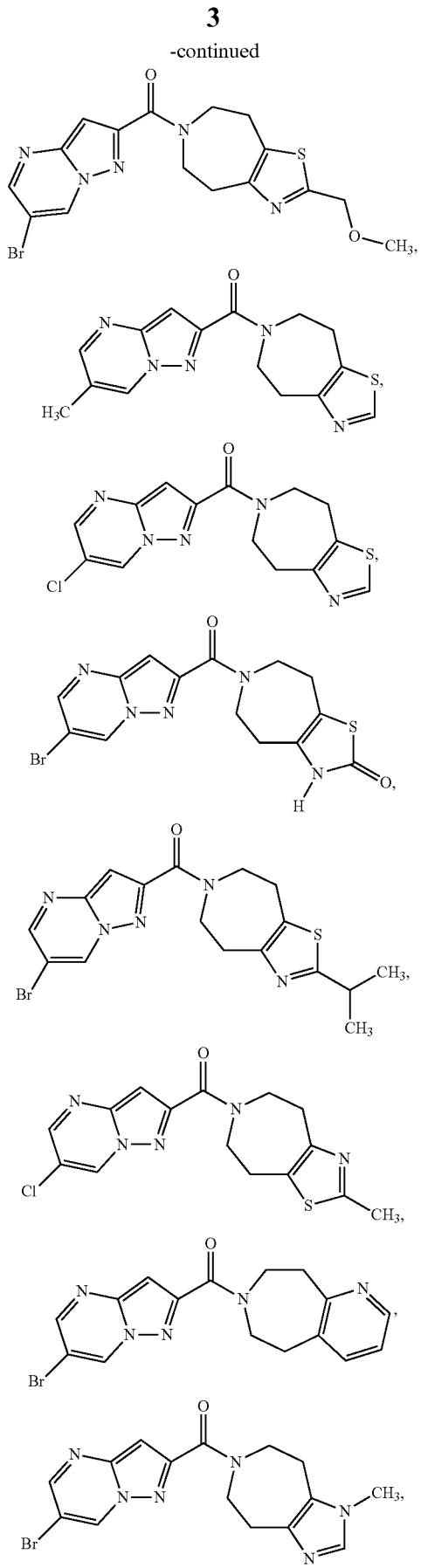

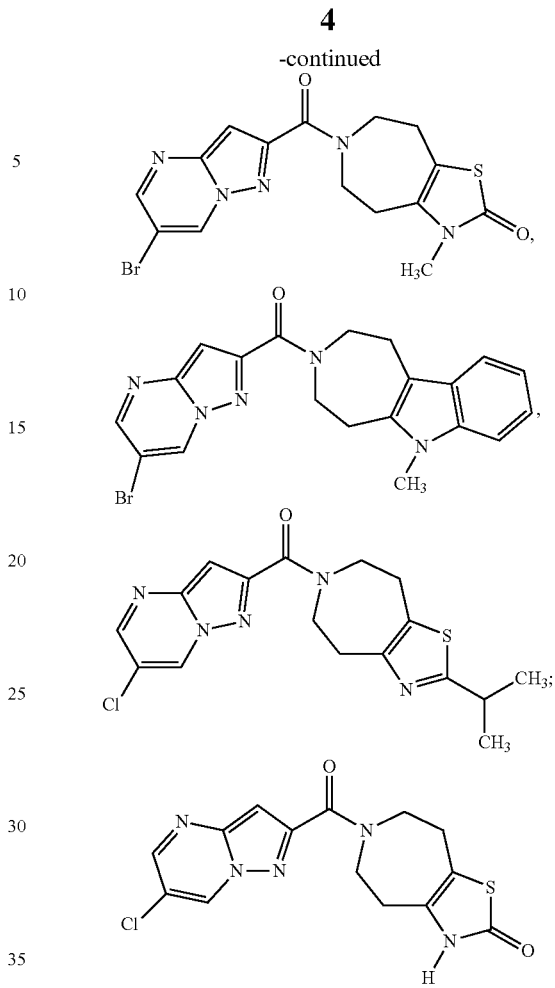

or a pharmaceutically acceptable salt thereof.

Although, these compounds fall under the genus of WO2004/089471, most surprisingly they show practically no activity on 11β-hydroxysteroid dehydrogenase type 1 (11βHSD1), and more remarkably, they have surprisingly been found to act as antagonists of the metabotropic glutamate 5 receptor.

GENERAL DEFINITIONS

Terms not specifically defined herein should be given the meanings that would be given to them by one skill in the art in light of the disclosure and the context.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-di-chloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethane-sulfonic acid, 2-hydroxy-ethane-sulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoro acetate salts), also comprise a part of the invention.

BIOLOGICAL ASSAYS

The biological activity of compounds was determined by the following methods:
A. mGlu5 NAM FLIPR Assay (Assay 1)

Activation of the mGluR5 receptor expressed in cell lines results in an increase in intracellular calcium concentration. Using calcium sensitive fluorescent dyes and a suited fluorescence plate reader this functional response is detectable and quantifiable. This technique could be used to characterize pharmacological modifications of the mGluR5 receptor.

$[Ca]_i$ measurements were performed in HEK293 cells stably expressing the full-length human mGlu5a receptor under the control of a tet-regulated promoter. Cells were cultivated in Dulbecco's modified eagle's medium (DMEM) with 10% fetal calf serum, 100 µg/ml HygromycinB, 500 µg/ml G418 and 2 µg/ml Tetracycline in a 37°, 95% humidity and 5% CO2 incubator. Confluent cell cultures were split on a bi-weekly schedule.

72 hours prior to the assay run mGluR5a expression was induced by replacing the culture medium by DMEM with 10% fetal calf serum without antibiotics. 24 hours prior to the assay run, cell medium was replaced after two wash steps by DMEM, 10% fetal calf serum without glutamine and phenol red. On the assay day, cells were detached from the culture flask by versene, washed, resuspended in a modified Ringer solution with 5 mM Glucose and 10 mM HEPES pH7.4, and plated on Poly-D-Lysine coated 384-well plates with a density of 10.000 cells/60 µl per well. After a seeding time of 1 hour in the incubator the cells were dye-loaded by adding 20 µl of a 4-fold concentrated dye solution from the Calcium 4 kit (Molecular Devices Inc., R8141) according to the manufacturer's manual and incubated for an additional 100 minutes. Compounds were prepared by a 11 point serial dilution in DMSO and a final dilution step into assay puffer (modified Ringer) to ensure a final DMSO concentration of 1% in the assay.

Measurements were done in a two-step procedure. A first measurement was performed directly after the addition of compounds to the cell plates to quantify and correct for compound related non specific effects (e.g. auto fluorescence). 5 minutes later, the antagonistic activities of the compounds were measured by addition of a EC90 concentration of the agonist glutamate (the EC90 concentration was controlled by glutamate dose-response curves). All measurements were done with a fluorimetric imaging plate reader (FLIPR, Molecular Devices Inc.).

$IC_{50}$ values and Hill slopes were derived from 11-point four parametric non-linear curve fittings with the AssayExplorer software using peak heights of fluorescence signals.

The compounds of this invention or the physiological acceptable salts thereof were tested for their inhibitory effect on the enzyme 11β-hydroxysteroid dehydrogenase (HSD) 1.
B. 11β-hydroxysteroid dehydrogenase (HSD) 1 Assay (Assay 2)

In vitro inhibition of 11β-HSD1 was determined with HTRF (Homogeneous Time-Resolved Fluorescence) technology (cisbio international, France) detecting cortisol generated from cortisterone by human liver microsomes. Compounds were incubated for 1 hour at 37° C. in Tris buffer (20 mM tris, 5 mM EDTA, pH 6.0) containing NADPH (200 µM) and cortisone (80 nM). Cortisol generated in the reaction was then detected by a competitive immunoassay involving two HTRF conjugates: cortisol linked to XL665 and anticortisol antibody labeled with Europium cryptate. The incubation period for detection reaction was 2 hours. The amount of cortisol is determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0%

CTL; 'low values'). Each assay also comprised a calibration curve with cortisol to transform the fluorescent data into cortisol concentrations.

Percent inhibition (% CTL) of each compound is determined relative to the carbenoxolone signal and IC$_{50}$ curves were generated.

C. Biological Data

TABLE 1

Biological data of the compounds of the present invention as obtained in assays 1 and 2.

| Example | Structure/Name | mGlu5 FLIPR IC$_{50}$ [μM] | 11βHSD1 IC$_{50}$ [μM] |
|---|---|---|---|
| (1) | | 0.146 | >10 |
| (2) | | 0.230 | >10 |
| (3) | | 1.385 | >10 |
| (4) | | 0.033 | >10 |
| (5) | | 0.110 | >10 |
| (6) | | 0.043 | >10 |

TABLE 1-continued
Biological data of the compounds of the present invention as obtained in assays 1 and 2.
| Example | Structure/Name | mGlu5 FLIPR IC$_{50}$ [μM] | 11βHSD1 IC$_{50}$ [μM] |
|---|---|---|---|
| (7) | 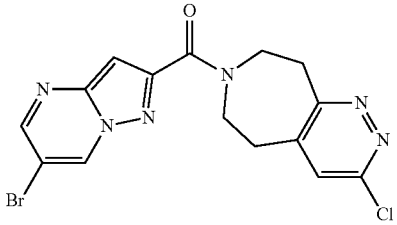 [SMILES: O=C(c1cc2ncc(Br)cn2n1)N1CCc2cc(Cl)nnc2CC1] | 0.340 | >10 |
| (8) | 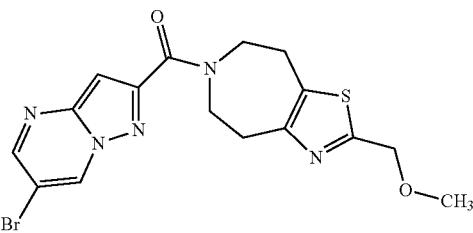 [SMILES: COCc1nc2c(s1)CCN(C(=O)c1cc3ncc(Br)cn3n1)CC2] | 1.545 | >10 |
| (9) | 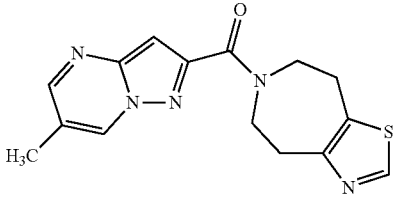 [SMILES: Cc1cnc2cc(C(=O)N3CCc4ncsc4CC3)nn2c1] | 1.42 | >10 |
| (10) | 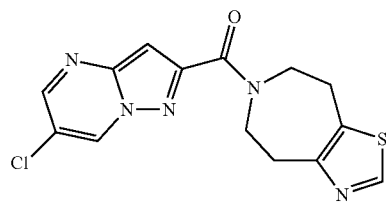 [SMILES: O=C(c1cc2ncc(Cl)cn2n1)N1CCc2ncsc2CC1] | 0.059 | >10 |
| (11) | 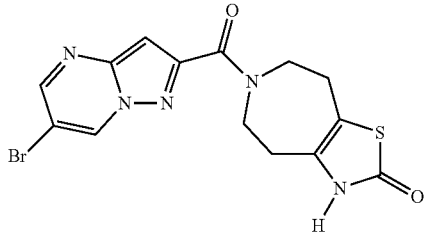 [SMILES: O=C(c1cc2ncc(Br)cn2n1)N1CCc2[nH]c(=O)sc2CC1] | 0.066 | >10 |
| (12) | 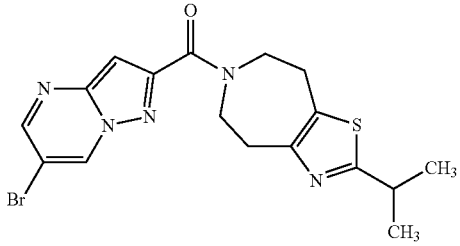 [SMILES: CC(C)c1nc2c(s1)CCN(C(=O)c1cc3ncc(Cl)cn3n1)CC2] | 0.148 | >10 |
| (13) | 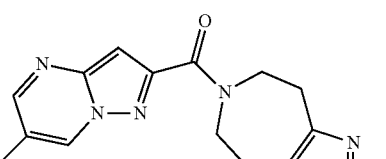 | 0.063 | >10 |

Table 2 reveals the relevant biological properties of compounds of the prior art WO 2004/089471 when assessed in assays 1 and 2 and thus demonstrates a comparison with the closest prior art. Data on compounds A and B, which were not disclosed in WO2004/089471 explicitly, also demonstrate inactivity of these compounds in both assays 1 and 2.

annelated to a 5-membered heterocyclic ring. Direct comparison of compounds of the present invention with compounds C, D and E demonstrates strikingly the unpredictability of the mGlu5 receptor inhibitory activity of pyrazolopyrimidines even if their structural differences are seemingly so small.

TABLE 2

Biological properties of selected compounds disclosed in or comprised by WO2004/089471

| Example number in WO2004/089471 | Structure/Name | mGlu5 FLIPR IC$_{50}$ [μM] | 11βHSD1 IC$_{50}$ [μM] |
|---|---|---|---|
| 4-21 | | >10 | >10 |
| 4-22 | | >10 | >10 |
| not disclosed explicitly | A | >10 | nt |
| not disclosed explicitly | B | >10 | >10 |

Table 3 shows data on pyrazolopyrimidines that are attached via an amide group to an azepane ring being further

TABLE 3

Biological properties of selected compounds comprised by WO2004/089471

| Comparison compound | Structure/Name | mGlu5 FLIPR IC$_{50}$ [μM] | 11βHSD1 IC$_{50}$ [μM] |
|---|---|---|---|
| C | (structure) | >10 | >10 |
| D | (structure) | >10 | >10 |
| E | (structure) | >10 | >10 |

Method of Treatment

The present invention is directed to compounds which are useful in the treatment and/or prevention of a disease, disorder and/or condition wherein the inhibition of the activity of the metabotropic glutamate 5 receptor is of therapeutic benefit, including but not limited to the treatment of psychiatric diseases, disorders or conditions; neurological diseases, disorders or conditions; and the treatment and/or prevention of pain diseases, disorders or conditions.

Preferably, the compounds of the present invention are useful for the treatment of psychiatric diseases, disorders or conditions selected from the group consisting of psychotic disorders, schizophrenia, depression and bipolar mood disorders, anxiety disorders, general anxiety disorder (GAD), panic, posttraumatic stress, phobia, acute stress, paranoia, obsessive or compulsive disorders, anorexia, bulimia, personality disorders, failure to thrive, sexual dysfunction, substance related disorders, disorders of impulse control, which latter two group of disorders including physical or emotional dependence upon or addiction to a substance (e.g. alcohol, nicotine, other drug substances) or activity (e.g. pathological gambling, binge eating, sexual activity).

Preferably, the compounds according to the invention are useful for the treatment of neurological diseases, disorders or conditions selected from the group consisting of epilepsy, Alzheimer's disease, cognitive disorders, memory deficits, Parkinson's disease, Aids related dementia, anoxic and ischemic injuries (stroke), attention deficit/hyperactivity disorder, delirium tremens, neurodegeneration, neurotoxicity, Fragile X, amyotrophic lateral sclerosis, Huntington's Choria, autism, mental retardation, Down's syndrome and head trauma.

Preferably, the compounds according to the invention are useful for the treatment, prevention or amelioration of pain diseases, disorders or conditions selected from the group consisting of chronic and acute migraine; neuralgia, postherpetic neuralgia, trigeminal neuralgia; chemotherapy induced neuropathies; inflammatory and neuropathic pain, diabetic neuropathy, arthritis, rheumatoid diseases, low back pain, post-operative pain, pain associated with other conditions such as angina, renal or billiary colic, menstruation, gout.

Accordingly, the present invention relates to a compound as a medicament.

Furthermore, the present invention relates to the use of the compounds for the treatment and/or prevention of a disease, disorder or condition wherein the inhibition of the activity of the metabotropic glutamate 5 receptor is of therapeutic benefit.

Furthermore, the present invention relates to the use of the compounds for the treatment of psychiatric diseases, disorders or conditions; neurological diseases, disorders or conditions; and for the treatment and/or prevention of pain diseases, disorders or conditions.

Preferably, the present invention relates to the use of the compounds for the treatment of psychiatric diseases, disorders or conditions selected from the group consisting of psychotic disorders, schizophrenia, depression and other mood disorders (bipolar), anxiety disorders (GAD, panic, posttraumatic stress, phobia, acute stress, paranoia), obsessive/compulsive disorders, anorexia/bulimia, personality disorders, failure to thrive or sexual dysfunction, substance related disorders, disorders of impulse control, which latter two group of disorders including physical or emotional dependence upon or addiction to a substance (e.g. alcohol, nicotine, other drug substances) or activity (e.g. pathological gambling, binge eating, sexual activity).

Preferably, the present invention relates to the use of the compounds for the treatment of neurological diseases, disorders or conditions selected from the group consisting of epilepsy, Alzheimer's disease, cognitive disorders, memory deficits, Parkinson's disease, Aids related dementia, anoxic and ischemic injuries (stroke), attention deficit/hyperactivity disorder, delirium tremens, neurodegeneration, neurotoxicity, Fragile X, amyotrophic lateral sclerosis, Huntington's Choria, autism, mental retardation, Down's syndrome and head trauma.

Preferably, the present invention relates to the use of the compounds for the treatment, prevention or amelioration of pain diseases, disorders or conditions selected from the group consisting of chronic and acute migraine; neuralgia (post-herpetic neuralgia, trigeminal neuralgia); chemotherapy induced neuropathies; inflammatory and neuropathic pain including diabetic neuropathy, arthritis, rheumatoid diseases, low back pain, post-operative pain, pain associated with other conditions (such as angina, renal or billiary colic, menstruation, gout). In a further aspect of the present invention the present invention relates to methods for the treatment and/or prevention of above mentioned diseases and conditions, which method comprises the administration of an effective amount of a compound of the invention to a human being.

The dose range of the compounds of the invention applicable per day is usually from 1 to 1000 mg, preferably from 5 to 800 mg, more preferably from 5 to 500 mg. Each dosage unit may conveniently contain from 1 to 1000 mg, preferably 1 to 500 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds of the present invention with known excipients, for example inert diluents, carriers, disintegrants, adjuvants, surfactants, binders and/or lubricants. The tablets may also consist of several layers.

Combination Therapy

The compounds according to the invention may also be used in conjunction with other active substances, particularly for the treatment, prevention or amelioration of diseases and conditions mentioned above. Other active substances which are suitable for such combinations include, for example, those which potentiate the therapeutic effect of a metabotropic glutamate 5 receptor antagonists according to the invention with respect to one of the indications mentioned and/or which allow the dosage of a metabotropic glutamate 5 receptor antagonist according to the invention to be reduced. Therapeutic agents which are suitable for such a combination include, for example H2 blocking agents (e.g. cimetidine, ranitidine), proton pump inhibitors such as pyridinylmethylsulfinyl benzimidazoles (e.g. omeprazole, esomeprazole, lansoprazole, pantoprazole, rabeprazole or related substances such as leminoprazole), anti-Alzheimers agents, such as beta-secretase inhibitors, gamma-secretase inhibitors, muscarinic agonists, muscarinic potentiators HMG-CoA reductase inhibitors, NSAIDs and anti-amyloid antibodies. The list also includes sedatives hypnotics, anxiolytics, antipsychotics, anti-epileptics, selective serotonin reuptake inhibitors, selective serotonin and norepihephrine reuptake inhibitors, tricyclic antidepressant drugs, monoamine oxidase inhibitors, 5-HT2 agonists or antagonists, GlyT1 inhibitors and the like such as, but not limited to risperidone, clozapine, olanzapine, haloperidol, fluoxetine, prazepam, sanomeline, lithium, phenobarbitol and salts thereof and combinations thereof.

Moreover, combinations with drugs like levodopa (with or without a selective extracerbral decarboxylase inhibitor), anti-cholinergics such as biperiden, COMT inhibitors such as entacapone, A2a adenosine antagonists, cholinergic agonists, NMDA receptor agonists or antagonists and dopamine agonists. The list further includes opiate agonists or antagonists, calcium channel antagonists, sodium channel antagonists, COX-2 selective inhibitors, NK1 antagonists, GABA-A receptor modulators, dopamine agonists or antagonists, norepinephrine modulators, nicotinic agonists or antagonists including nicotine, and muscarinic agonists or antagonists. Therapeutic agents which are also suitable for such a combination include, for example methadone, levo-alpha-acetylmathdol, buprenorphine and naltrexone, disulfuram and acamprosate, Buspirone, valproate and gabapentin.

EXPERIMENTAL PART

The hereinafter described compounds have been characterized through their characteristic mass after ionisation in a mass-spectrometer, their Rf-value on thin-layer-chromatography plate and/or their retention time on an analytical HPLC.

List of Abbreviations

ACN acetonitrile
AcOH acetic acid
aq. aqueous
BOC tert-butoxy-carbonyl-
° C. degree celsius
DCM dichloromethane
DIPEA N,N-diisopropylethylamine
DMF N,N-dimethylformamide
DMSO dimethyl sulfoxide
EI-MS electron induced mass spectrometry
ESI-MS electrospray ionisation mass spectrometry
EtOAc ethyl acetate
EtOH ethanol
h hour HATU 2-(1H-7-azabenzotriazol-1-yl)-1,1,3,3-tetramethyluronium hexafluorophosphate
HOBt N-hydroxybenzotriazole
HPLC high performance liquid chromatography
L liter
MeOH methanol
min minute
mL milliliter
MS mass spectrum
n.d. not determined
NH4OH ammoniac
NMP N-methyl-2-pyrrolidone
Pd/C palladium on activated carbon
psi pound per square inch
$R_f$ retention factor
RT room temperature (about 20° C.)
$R_t$ retention time
TEA triethylamine
TF/TFA trifluoroacetic acid
THF tetrahydrofuran
TBTU 2-(1H-benzotriazol-1-yl)-1,1,3,3-tetramethyluronium tetrafluoroborat
TLC thin layer chromatography HPLC Methods Columns:

| | |
|---|---|
| S2 | Zorbax-column (Agilent Technologies), SB (Stable Bond) C18; 1.8 µm; 3.0 × 30 mm |
| S4 | X-Bridge (Waters) C18; 2.5 µm; 3.0 × 30 mm, |
| S6 | X-Bridge (Waters) C18; 3.5 µm; 4.6 × 30 mm, |

Solvent Systems:
Gradient 1 (G1):
Solvent A: Water (with 0.1% formic acid)
Solvent B: Acetonitrile (mit 0.1% formic acid)
HPLC system: Agilent 1100 with DA- and MS-detector
Gradient (room temperature):

| Gradient | Zeit [min] | % A | % B |
|---|---|---|---|
| G1 | 0.00 | 95 | 5 |
| (1.6 mL/min) | 0.10 | 95 | 5 |
| | 1.75 | 5 | 95 |
| | 1.90 | 5 | 95 |
| | 1.95 | 95 | 5 |
| | 2.00 | 95 | 5 |

Gradient 2 (G2):
Solvent A: Water (with 0.1% trifluoracetic acid)
Solvent B: Methanol (with 0.1% trifluoracetic acid)
HPLC system: Agilent 1100 with DA- and MS-detector
Gradient (temperature 60° C.)

| Gradient | time [min] | % A | % B |
|---|---|---|---|
| G2 | 0.00 | 95 | 5 |
| (4 mL/min) | 0.15 | 95 | 5 |
| | 1.70 | 0 | 100 |
| | 2.25 | 0 | 100 |

Gradient 3 (G3):
Solvent A: Water (with 0.1% trifluoracetic acid)
Solvent B: Methanol
HPLC system: Agilent 1200 with DA- and MS-detector
Gradient (temperature 60° C.)

| Gradient | time [min] | % A | % B |
|---|---|---|---|
| G3 | 0.00 | 95 | 5 |
| (2.2 mL/min) | 0.05 | 95 | 5 |
| | 1.40 | 0 | 100 |
| | 1.80 | 0 | 100 |

Gradient 4 (G4):
Solvent A: Water (with 0.1% NH4OH)
Solvent B: Methanol
HPLC system: Agilent 1200 with DA- and MS-detector, Gradient (temperature 60° C.)

| Gradient | time [min] | % A | % B |
|---|---|---|---|
| G4 | 0.00 | 95 | 5 |
| (2.2 mL/min) | 0.05 | 95 | 5 |
| | 1.40 | 0 | 100 |
| | 1.80 | 0 | 100 |

Gradient 5 (G5):
Solvent A: water (with 0.2% NH4OH)
Solvent B: methanol (with 3% water)
HPLC system: Agilent with DA- and MS-detector
Gradient (temperature RT)

| Gradient | time [min] | % A | % B |
|---|---|---|---|
| G5 | 0.00 | 95 | 5 |
| (1.0 mL/min) | 0.20 | 95 | 5 |
| | 2.80 | 5 | 95 |
| | 3.0 | 5 | 95 |
| | 3.10 | 0 | 100 |
| | 3.80 | 0 | 100 |

Methods:
The HPLC methods are a combination from a gradient and a column.

| | Column | Gradient |
|---|---|---|
| Methode B | S2 | G1 |
| Method J | S6 | G2 |
| Method K | S4 | G4 |
| Method L | S4 | G1 |
| Method M | S4 | G3 |
| Method N | S2 | G3 |
| Method O | S4 | G5 |

Preparation of Intermediates

Intermediate 1

5-Bromo-azepan-4-one hydrobromide

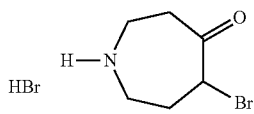

32.2 mL (0.37 mol) Hydrobromic acid (62%) in 50 mL acetic acid were added dropwise to 50.0 g (0.33 mol) hexahydro-4H-azepin-4-one hydrochloride in 0.6 L acetic acid. 17 mL (0.34 mol) bromine in 50 mL acetic acid were added dropwise and the reaction was stirred at room temperature (RT). Then reaction was concentrated and the residue was crystallized with acetonitrile.

Yield: 79.0 g (87% of theory)
ESI-MS: m/z=192 (M+H)$^+$
R$_t$(HPLC): 0.64 min (method B)

Intermediate 2

2-Ethyl-5,6,7,8-tetrahydro-4H-thiazolo[4,5-d]azepine hydrobromide

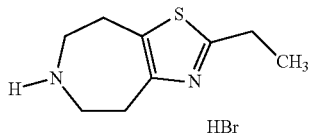

0.40 g (1.47 mmol) 5-bromo-azepan-4-one hydrobromide, 0.13 g (1.47 mmol) thiopropionamide and 3 mL ethanol were stirred under reflux for 3 hours. The reaction was allowed to cool to RT and was filtered. The filtrate was concentrated to dryness and dried.

Yield: 0.39 g (quantitativ)
ESI-MS: m/z=183 (M+H)$^+$
R$_t$(HPLC): 0.39 min (Method J)

Intermediate 3

2-Methoxy-5,6,7,8-tetrahydro-4H-thiazolo[4,5-d]azepine trifluoroacetate

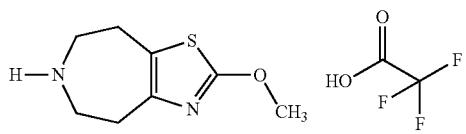

Step 1: 2-Amino-4,5,7,8-tetrahydro-thiazolo[4,5-d]azepine-6-carboxylic acid tert-butyl ester

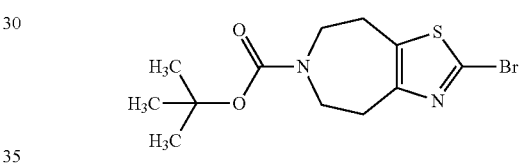

2.5 g (7.55 mmol) 5,6,7,8-Tetrahydro-4H-thiazolo[4,5-d]azepin-2-ylamine dihydrobromide, 1.83 g (8.31 mmol) di-tert.butyl-dicarbonat, 2.1 mL (15.1 mmol) in 60 mL tetrahydrofuran (THF) were stirred at 5° C. for 30 min and afterwards stirred at RT over night. The solvent was removed, the residue dissolved in ethyl acetate and washed several times with water. The aqueous layer was washed with ethyl acetate. The combined organic layers were dried, filtered and evaporated to dryness. The residue war cristallized with petrol ether. Yield: 1.20 g (59% of theory). ESI-MS: m/z=270 (M+H)$^+$.

Step 2: 2-Bromo-4,5,7,8-tetrahydro-thiazolo[4,5-d]azepine-6-carboxylic acid tert-butyl ester

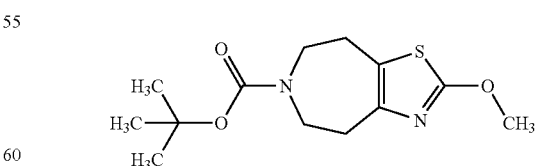

1.70 mL (15 mmol) tert-Butyl-nitrite was added to 3.31 g (15 mmol) copper-(II)-bromide in 100 mL ACN and stirred at RT for 10 min. The reaction mixture was stirred at 60° C. and 2.00 g (7.43 mmol) 2-amino-4,5,7,8-tetrahydro-thiazolo[4,5-d]azepine-6-carboxylic acid tert-butyl ester was added and the reaction was stirred for 1 h at 60° C. The reaction was concentrated to dryness and ethylacetate and water were added to the residue. After filtration the organic layer was separated, dried and concentrated to dryness. The residue was purified by chromatography.

Yield: 1.26 g (51% of theory)
ESI-MS: m/z=333 (M+H)$^+$

Step 3: 2-Methoxy-4,5,7,8-tetrahydro-thiazolo[4,5-d]azepine-6-carboxylic acid tert-butyl ester 1.00 g (3.00 mmol) bromo-4,5,7,8-tetrahydro-thiazolo[4,5-d]azepine-6-carboxylic acid tert-butyl ester, 0.40 g (7.00 mmol) sodium methylate in 15 mL methanol were heated at 100° C. for 4 h under microwave irradiation. The mixture was purified by chromatography.

Yield: 0.40 g (47% of theory), $R_t$(HPLC): 1.49 min (Method J)

Step 4: 2-Methoxy-5,6,7,8-tetrahydro-4H-thiazolo[4,5-d]azepine trifluoroacetate and 3,4,5,6,7,8-Hexahydro-thiazolo[4,5-d]azepin-2-one trifluoro acetate

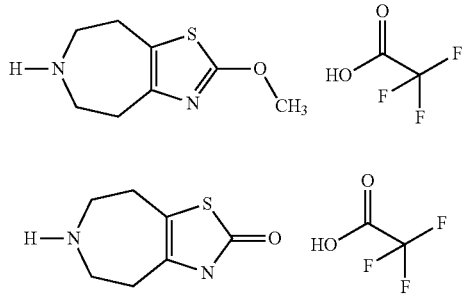

0.40 g (1.4 mmol) 2-methoxy-4,5,7,8-tetrahydro-thiazolo[4,5-d]azepine-6-carboxylic acid tert-butyl ester, 1.3 mL trifluoroacetic acid in 2.5 mL dichloromethane (DCM) were stirred at RT overnight. The reaction was concentrated to dryness. DCM and a small amount of methanol (MeOH) were added to the residue and filtrated. The precipitate were isolated and 90 mg 3,4,5,6,7,8-Hexahydro-thiazolo[4,5-d]azepin-2-one trifluoro-acetic acid was obtained. Yield: 90 mg (23% of theory). ESI-MS: m/z=171 (M+H)$^+$; $R_t$(HPLC): 0.15 min (Method J).

The filtrate was concentrated to dryness and 80 mg of 2-Methoxy-5,6,7,8-tetrahydro-4H-thiazolo[4,5-d]azepine trifluoroacetate was obtained. Yield: 80 mg (19% of theory). ESI-MS: m/z=185 (M+H)$^+$; $R_t$(HPLC): 0.19 min (Method J).

Intermediate 4

2-Methyl-5,6,7,8-tetrahydro-4H-thiazolo[4,5-d]azepine hydrochloride

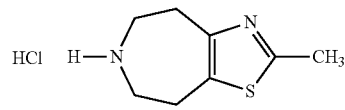

20.0 g (73.3 mmol) 5-Bromo-azepan-4-one hydrobromide, 5.5 g (73.3 mmol) thioacetamide in 140 mL ethanol were stirred under reflux for 4 h. After cooling to 0° C. the reaction was filtered. The precipitate was collected and MeOH was added. After filtration the solvent was removed. The residue was cooled and ethereal hydrochloric acid was added and filtrated. The precipitate was collected, washed with diisopropylether and dried. Yield: 11.0 g (70% of theory). ESI-MS: m/z=169 (M+H)$^+$, $R_t$(HPLC): 0.33 min (Method B).

Intermediate 5

3-Chloro-6,7,8,9-tetrahydro-5H-1,2,7-triaza-benzo-cycloheptene trifluoro-acetate

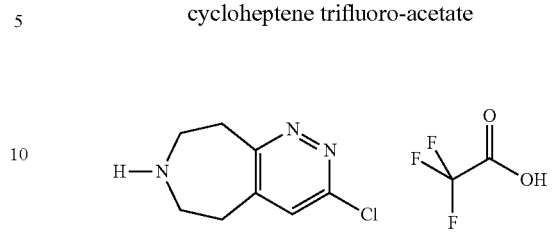

0.15 g (0.53 mmol) 3-chloro-5,6,8,9-tetrahydro-1,2,7-triaza-benzocycloheptene-7-carboxylic acid tert-butyl ester (CAS: 1251001-53-2), 0.4 mL trifluoroacetic acid and 2 mL DCM were stirred at RT for 4 hours. The reaction was concentrated to dryness. Yield: 0.16 g (quantitativ). ESI-MS: m/z=184/186 (M+H)$^+$; $R_t$(HPLC): 0.41 min (Method K).

Intermediate 6

2-Methoxymethyl-5,6,7,8-tetrahydro-4H-thiazolo[2,3-d]azepine hydrobromide

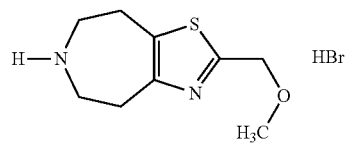

0.40 g (1.47 mmol) 5-Bromo-azepan-4-one hydrobromide, 0.15 mg (1.47 mmol) 2-methoxy-thioacetamide in 3 mL ethanol were stirred under reflux for 3 h. The reaction mixture was diluted with ethanol and the precipitate was removed. The filtrate was concentrated to dryness. The residue was used without further purification. Yield: 0.20 g (49% of theory). ESI-MS: m/z=199 (M+H)$^+$; $R_t$(HPLC): 0.52 min (Method J).

Intermediate 7

5,6,7,8-Tetrahydro-4H-thiazolo[4,5-d]azepine hydrochloride

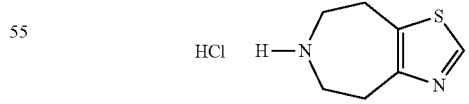

Under a nitrogen atmosphere 1.7 g (12.3 mmol) 1-chloroethyl chloroformate was added to 2.0 g (8.2 mmol) 6-benzyl-5,6,7,8-tetrahydro-4H-thiazolo[4,5-d]azepine (CAS Registry Number: 1159094-24-2) in 20 mL DCM at 0° C. The reaction mixture was stirred at RT for 2 h. The reaction mixture was concentrated and 20 mL anhydrous methanol was added. The reaction mixture was stirred under reflux for 1 h and concentrated. The resulting crude product was washed with DCM, the solid was filtered and dried. Yield: 0.35 g (58% of theory). ESI-MS: m/z=199 (M+H)⁺; $R_f$(HPLC): 0.52 min (Method J).

Intermediate 8

2-Isopropyl-5,6,7,8-tetrahydro-4H-thiazolo[4,5-d]azepine

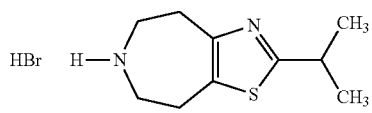

0.4 g (1.47 mmol) 5-Bromo-azepan-4-one hydrobromide, 0.15 g (1.47 mmol) thioisobutyramide in 3 mL ethanol were stirred under reflux for 3 h. The reaction mixture was concentrated and to the residue DCM and a small amount of methanol were added. The precipitate was removed and the filtrate was evaporated to dryness. Yield: 0.36 g (89% of theory). ESI-MS: m/z=197 (M+H)⁺; $R_f$(HPLC): 0.79 min (Method J).

Intermediate 9

6,7,8,9-Tetrahydro-5H-pyrido[2,3-d]azepine

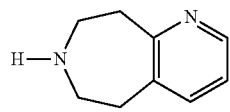 [SMILES: c1cnc2c(c1)CCNCC2]

Under a hydrogen atmosphere 0.125 g (0.49 mmol) 2-chloro-6,7,8,9-tetrahydro-5H-pyrido[2,3-d]azepine, 30 mg palladium on charcoal (10%) and 0.28 mL triethylamine in 4 mL methanol were hydrogenated at RT under 50 psi hydrogen pressure for 6 h. The catalyst was removed and the filtrate was concentrated to dryness. The residue was used without further purification. Yield: 72 mg (99% of theory). ESI-MS: m/z=149 (M+H)⁺; $R_f$(HPLC): 0.52 min (Method J).

Methods of Preparation of Compounds

Example 1

(6-Bromo-pyrazolo[1,5-a]pyrimidin-2-yl)-(2-chloro-5,6,8,9-tetrahydro-pyrido[2,3-d]azepin-7-yl)-methanone

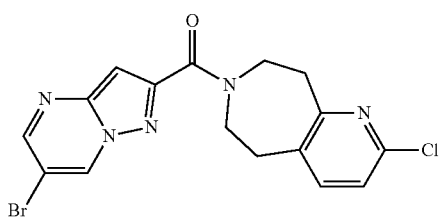 [SMILES: O=C(c1cc2ncc(Br)cn2n1)N1CCc2ccc(Cl)nc2CC1]

To 0.03 g (0.12 mmol) 6-bromo-pyrazolo[1,5-A]pyrimidine-2-carboxylic acid, 0.12 mmol 2-chloro-6,7,8,9-tetrahydro-5H-pyrido[2,3-d]azepine hydrochloride and 0.51 mmol triethyl amine (TEA) in 1.5 ml dimethylformamide (DMF) 0.14 mmol TBTU (O-(Benzotriazol-1-yl)-N,N,N',N'-tetramethyluronium tetrafluoroborate) was added and the reaction mixture was stirred at RT for 1 h. Water was added to the reaction mixture. The precipitate was collected and dried. Yield: 0.018 g (36% of theory). ESI-MS: m/z=406 (M+H)⁺; $R_f$(HPLC): 1.29 min. (Method J).

Example 2

(6-Bromo-pyrazolo[1,5-a]pyrimidin-2-yl)-(2-methoxy-5,6,8,9-tetrahydro-pyrido[2,3-d]azepin-7-yl)-methanone

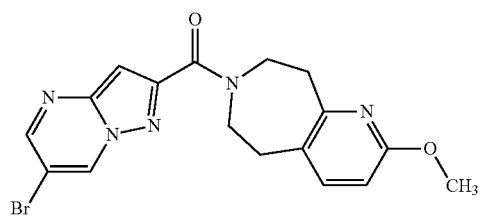 [SMILES: COc1ccc2c(n1)CCN(C(=O)c1cc3ncc(Br)cn3n1)CC2]

The title compound was prepared in accordance with the general method of example 2 from 6-bromo-pyrazolo[1,5-A]pyrimidine-2-carboxylic acid and 2-methoxy-6,7,8,9-tetrahydro-5H-pyrido[2,3-d]azepine. Yield: 0.05 g (60% of theory). ESI-MS: m/z=402 (M+H)⁺; $R_f$(HPLC): 1.12 min. (Method J).

Example 3

(6-Bromo-pyrazolo[1,5-a]pyrimidin-2-yl)-(4,5,7,8-tetrahydro-thieno[2,3-d]azepin-6-yl)-methanone

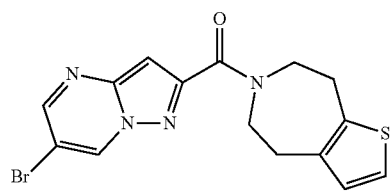 [SMILES: O=C(c1cc2ncc(Br)cn2n1)N1CCc2ccsc2CC1]

The title compound was prepared in accordance with the general method of example 1 from 6-bromo-pyrazolo[1,5-A]pyrimidine-2-carboxylic acid and 5,6,7,8-tetrahydro-4H-thieno[2,3-d]azepine. Yield: 56 mg (72% of theory). ESI-MS: m/z=377 (M+H)⁺; $R_f$(HPLC): 1.41 min (Method B).

Example 4

(6-Bromo-pyrazolo[1,5-a]pyrimidin-2-yl)-(2-ethyl-4,5,7,8-tetrahydro-thiazolo[4,5-d]azepin-6-yl)-methanone

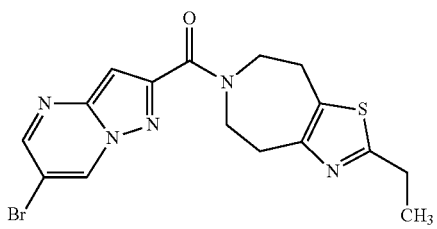 [SMILES: CCc1nc2c(s1)CCN(C(=O)c1cc3ncc(Br)cn3n1)CC2]

The title compound was prepared in accordance with the general method of example 1 from 6-bromo-pyrazolo[1,5-A]pyrimidine-2-carboxylic acid and 2-ethyl-5,6,7,8-tetrahydro-4H-thiazolo[4,5-d]azepine hydrobromide. The reaction mixture was purified by HPLC chromatography and lyophilized. Yield: 24 mg (29% of theory). ESI-MS: m/z=406 (M+H)$^+$; R$_t$(HPLC): 1.19 min. (Method J).

Example 5

(6-Bromo-pyrazolo[1,5-a]pyrimidin-2-yl)-(4,5,7,8-tetrahydro-thiazolo[4,5-d]azepin-6-yl)-methanone

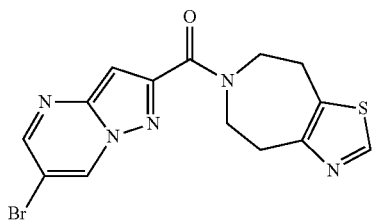 [SMILES: O=C(c1cc2ncc(Br)cn2n1)N1CCc2ncsc2CC1]

The title compound was prepared in accordance with the general method of example 1 from 6-bromo-pyrazolo[1,5-A]pyrimidine-2-carboxylic acid and 5,6,7,8-tetrahydro-4H-thiazolo[4,5-d]azepine. The reaction mixture was purified by HPLC chromatography and lyophilized. Yield: 27 mg (35% of theory). ESI-MS: m/z=378 (M+H)$^+$; R$_t$(HPLC): 1.08 min. (Method B).

Example 6

(6-Bromo-pyrazolo[1,5-a]pyrimidin-2-yl)-(2-methyl-4,5,7,8-tetrahydro-3H-1lambda*4*-thiazolo[4,5-d]azepin-6-yl)-methanone

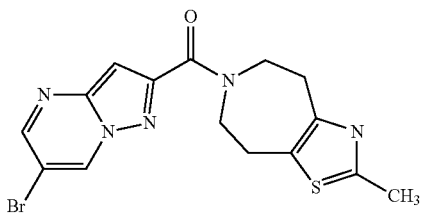

The title compound was prepared in accordance with the general method of example 1 from 6-bromo-pyrazolo[1,5-A]pyrimidine-2-carboxylic acid and 2-methyl-5,6,7,8-tetrahydro-4H-thiazolo[4,5-d]azepine hydrochloride. The reaction mixture was purified by HPLC chromatography and lyophilized. Yield: 13 mg (16% of theory). ESI-MS: m/z=392 (M+H)$^+$;

R$_t$(HPLC): 1.59 min. (Method O).

Example 7

(6-Bromo-pyrazolo[1,5-a]pyrimidin-2-yl)-(3-chloro-5,6,8,9-tetrahydro-1,2,7-triaza-benzocyclohepten-7-yl)-methanone

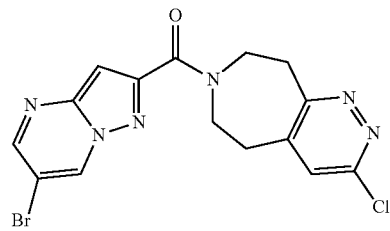 [SMILES: O=C(c1cc2ncc(Br)cn2n1)N1CCc2cc(Cl)nnc2CC1]

The title compound was prepared in accordance with the general method of example 1 from 6-bromo-pyrazolo[1,5-A]pyrimidine-2-carboxylic acid and 3-chloro-6,7,8,9-tetrahydro-5H-1,2,7-triaza-benzocycloheptene trifluoroacetate. The reaction mixture was purified by HPLC chromatography and lyophilized. Yield: 27 mg (32% of theory). ESI-MS: m/z=407 (M+H)$^+$; R$_t$(HPLC): 1.10 min. (Method J).

Example 8

(6-Bromo-pyrazolo[1,5-a]pyrimidin-2-yl)-(2-methoxymethyl-4,5,7,8-tetrahydro-thiazolo[4,5-d]azepin-6-yl)-methanone

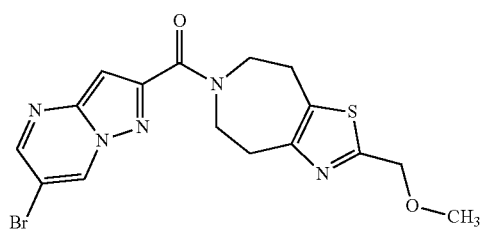 [SMILES: COCc1nc2c(s1)CCN(C(=O)c1cc3ncc(Br)cn3n1)CC2]

The title compound was prepared in accordance with the general method of example 1 from 6-bromo-pyrazolo[1,5-A]pyrimidine-2-carboxylic acid and 2-methoxymethyl-5,6,7,8-tetrahydro-4H-thiazolo[2,3-d]azepine, hydrobromide. The reaction mixture was purified by HPLC chromatography and lyophilized. Yield: 7 mg (8% of theory). ESI-MS: m/z=422 (M+H)$^+$; R$_t$(HPLC): 1.25 min. (Method J).

Example 9

(6-Methyl-pyrazolo[1,5-a]pyrimidin-2-yl)-4,5,7,8-tetrahydro-thiazolo[4,5-d]azepin-6-yl)-methanone

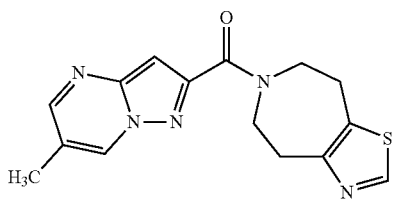 [SMILES: Cc1cnc2cc(C(=O)N3CCc4ncsc4CC3)nn2c1]

To 0.05 g (0.28 mmol) 6-methyl-pyrazolo[1,5-A]pyrimidine-2-carboxylic acid, 0.05 g (0.28 mmol) 5,6,7,8-tetrahydro-4H-thiazolo[4,5-d]azepine hydrochlorid and 0.12 mL (0.88 mmol) TEA in 1.5 mL DMF 0.1 g (0.31 mmol) TBTU was added and the reaction mixture was stirred at RT overnight. The reaction mixture was purified by HPLC chromatography and lyophilized. Yield: 43 mg (49% of theory). ESI-MS: m/z=314 (M+H)$^+$; R$_t$(HPLC): 0.97 min. (Method J).

Example 10

(6-Chloro-pyrazolo[1,5-a]pyrimidin-2-yl)-(4,5,7,8-tetrahydro-thiazolo[4,5-d]azepin-6-yl)-methanone

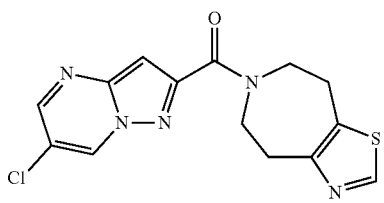 [SMILES: O=C(c1cc2ncc(Cl)cn2n1)N1CCc2ncsc2CC1]

0.19 mL (0.33 mmol, 50%) propane phosphonic acid anhydride was added to 50.0 mg (0.25 mmol) 6-chloropyrazolo[1,5-A]pyrimidine-2-carboxylic acid, 39 mg (0.25 mmol) 5,6,7,8-tetrahydro-4H-thiazolo[4,5-d]azepine and 0.12 mL (0.89 mmol) TEA in 1.5 mL DMF and stirred at RT overnight. The reaction mixture was purified by chromatography and lyophilized. Yield: 17 mg (20% of theory). ESI-MS: m/z=334 (M+H)$^+$, R$_t$(HPLC): 0.79 min (Method M).

Example 11

6-(6-Bromo-pyrazolo[1,5-a]pyrimidine-2-carbonyl)-3,4,5,6,7,8-hexahydro-thiazolo[4,5-d]azepin-2-one

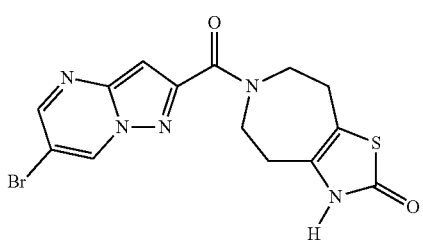 [SMILES: O=C(c1cc2ncc(Br)cn2n1)N1CCc2[nH]c(=O)sc2CC1]

The title compound was prepared in accordance with the general method of example 1 from 6-Bromo-pyrazolo[1,5-A]pyrimidine-2-carboxylic acid and 3,4,5,6,7,8-hexahydro-thiazolo[4,5-d]azepin-2-one. The reaction mixture was purified by HPLC chromatography and lyophilized. Yield: 40 mg (49% of theory). ESI-MS: m/z=394 (M+H)$^+$; R$_t$(HPLC): 1.11 min. (Method J).

Example 12

(6-Bromo-pyrazolo[1,5-a]pyrimidin-2-yl)-(2-isopropyl-4,5,7,8-tetrahydro-thiazolo[4,5-d]azepin-6-yl)-methanone

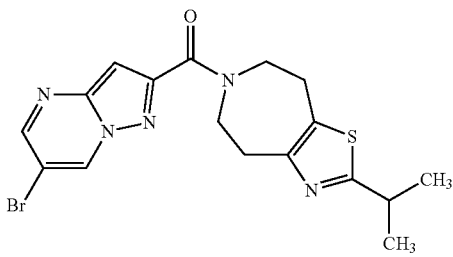 [SMILES: CC(C)c1nc2c(s1)CCN(C(=O)c1cc3ncc(Br)cn3n1)CC2]

The title compound was prepared in accordance with the general method of example 1 from 6-bromo-pyrazolo[1,5-A]pyrimidine-2-carboxylic acid and 2-isopropyl-5,6,7,8-tetrahydro-4H-thiazolo[4,5-d]azepine hydrobromide. The reaction mixture was purified by HPLC chromatography and lyophilized. Yield: 15 mg (17% of theory). ESI-MS: m/z=420 (M+H)$^+$; R$_t$(HPLC): 1.34 min. (Method J).

Example 13

(6-Chloro-pyrazolo[1,5-a]pyrimidin-2-yl)-(2-methyl-4,5,7,8-tetrahydro-thiazolo[4,5-d]azepin-6-yl)-methanone

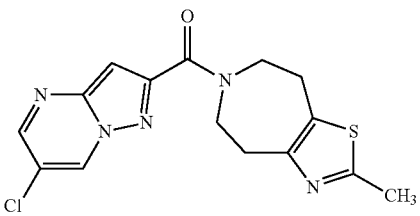 [SMILES: Cc1nc2c(s1)CCN(C(=O)c1cc3ncc(Cl)cn3n1)CC2]

0.72 g (2.23 mmol) TBTU was added to 0.40 g (2.03 mmol) 6-Chloro-pyrazolo[1,5-a]pyrimidine-2-carboxylic acid, 0.41 g (2.03 mmol) 2-Methyl-5,6,7,8-tetrahydro-4H-thiazolo[4,5-d]azepine hydrochloride and 0.88 mL (6.28 mmol) TEA in 8.0 mL DMF and stirred at RT overnight. The reaction mixture was purified by HPLC chromatography and lyophilized. Yield: 0.18 g (25% of theory). ESI-MS: m/z=348 (M+H)$^+$; R$_t$(HPLC): 1.01 min. (Method J).

Example 14

(6-Bromo-pyrazolo[1,5-a]pyrimidin-2-yl)-(5,6,8,9-tetrahydro-pyrido[2,3-d]azepin-7-yl)-methanone

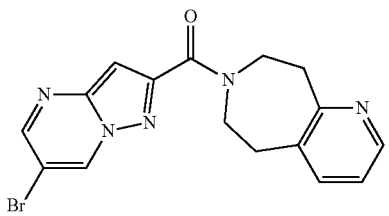 [SMILES: O=C(c1cc2ncc(Br)cn2n1)N1CCc2cccnc2CC1]

73 mg (0.23 mmol) TBTU was added to 50 mg (0.21 mmol) 6-Bromo-pyrazolo[1,5-a]pyrimidine-2-carboxylic acid, 31 mg (0.21 mmol) 6,7,8,9-Tetrahydro-5H-pyrido[2,3-d]azepine and 90 μL (0.64 mmol) TEA in 1.5 mL DMF and stirred at RT overnight. The reaction mixture was purified by HPLC chromatography and lyophilized. Yield: 22 mg (29% of theory). ESI-MS: m/z=372 (M+H)$^+$; R$_t$(HPLC): 0.81 min. (Method J).

Example 15

(6-Bromo-pyrazolo[1,5-a]pyrimidin-2-yl)-(1-methyl-4,5,7,8-tetrahydro-1H-imidazo[4,5-d]azepin-6-yl)-methanone

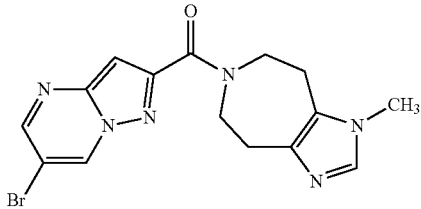 [SMILES: Cn1cnc2c1CCN(C(=O)c1cc3ncc(Br)cn3n1)CC2]

75.0 mg (0.21 mmol) 6 (6-Bromo-pyrazolo[1,5-a]pyrimidin-2-yl)-(4,5,7,8-tetrahydro-1H-imidazo[4,5-d]azepin-6-yl)-methanone, 13.0 μL (0.21 mmol) methyliodide, 35.0 mg (0.25 mmol) potassium carbonate in 1.0 mL DMF were stirred at RT overnight. The reaction mixture was purified by HPLC chromatography and lyophilized. Yield: 12 mg (15% of theory). ESI-MS: m/z=375 (M+H)$^+$; R$_t$(HPLC): 0.71 min. (Method K).

Example 16

6-(6-Bromo-pyrazolo[1,5-a]pyrimidine-2-carbonyl)-3-methyl-3,4,5,6,7,8-hexahydro-thiazolo[4,5-d]azepin-2-one

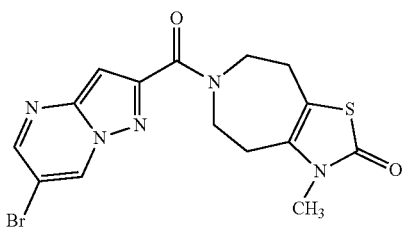 [SMILES: Cn1c2c(sc1=O)CCN(C(=O)c1cc3ncc(Br)cn3n1)CC2]

30.0 mg (0.076 mmol) 6-(6-bromo-pyrazolo[1,5-a]pyrimidine-2-carbonyl)-3,4,5,6,7,8-hexahydro-thiazolo[4,5-d]azepin-2-one, 6.3 μL (0.099 mmol) methyliodide, 3.7 mg (0.084 mmol) sodium hydride (50%) in 1.0 mL DMF were stirred at RT for 1 h. The reaction mixture was purified by HPLC chromatography and lyophilized. Yield: 5 mg (16% of theory). ESI-MS: m/z=408 (M+H)$^+$; R$_t$(HPLC): 0.95 min. (Method N).

Example 17

(6-Bromo-pyrazolo[1,5-a]pyrimidin-2-yl)-(6-methyl-1,4,5,6-tetrahydro-2H-azepino[4,5-b]indol-3-yl)-methanone

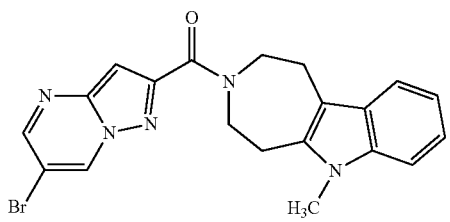 [SMILES: Cn1c2c(c3ccccc31)CCN(C(=O)c1cc3ncc(Br)cn3n1)CC2]

The title compound was prepared in accordance with the general method of example 1 from 6-bromo-pyrazolo[1,5-A]pyrimidine-2-carboxylic acid (0.10 mmol) and 6-methyl-1,2,3,4,5,6-hexahydro-azepine[4,5-d]indole hydrochloride. (0.10 mmol) in 1.5 mL DMF. Yield: 30 mg (69% of theory). ESI-MS: m/z=424 (M+H)$^+$; R$_t$(HPLC): 1.53 min. (Method J).

Example 18

(6-Chloro-pyrazolo[1,5-a]pyrimidin-2-yl)-(2-isopropyl-4,5,7,8-tetrahydro-thiazolo[4,5-d]azepin-6-yl)-methanone

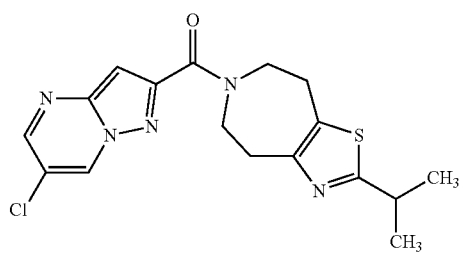 [SMILES: CC(C)c1nc2c(s1)CCN(C(=O)c1cc3ncc(Cl)cn3n1)CC2]

The title compound was prepared in accordance with the general method of example 1 from 0.25 mmol 6-chloro-pyrazolo[1,5-A]pyrimidine-2-carboxylic acid, 0.30 mmol HATU, 1.27 mmol DIPEA and 0.51 mmol 2-isopropyl-5,6,7,8-tetrahydro-4H-thiazolo[4,5-d]azepine in 1 mL DMF. The reaction mixture was purified by HPLC chromatography and lyophilized. Yield: 24 mg (25% of theory). ESI-MS: m/z=376 (M+H)⁺.

Example 19

6-(6-Chloro-pyrazolo[1,5-a]pyrimidine-2-carbonyl)-3,4,5,6,7,8-hexahydro-thiazolo[4,5-d]azepin-2-one

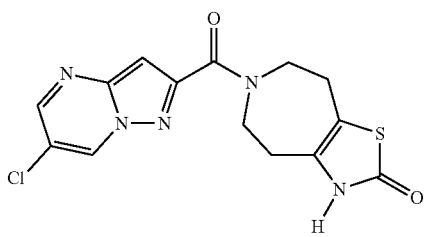 [SMILES: O=C(c1cc2ncc(Cl)cn2n1)N1CCc2[nH]c(=O)sc2CC1]

The title compound was prepared in accordance with the general method of example 1 from 0.25 mmol 6-chloro-pyrazolo[1,5-A]pyrimidine-2-carboxylic acid, 0.30 mmol HATU, 1.52 mmol DIPEA and 0.51 mmol 3,4,5,6,7,8-hexahydro-thiazolo[4,5-d]azepin-2-one in 1 mL DMF. The reaction mixture was purified by HPLC chromatography and lyophilized. Yield: 20 mg (23% of theory). ESI-MS: m/z=350 (M+H)⁺.

The invention claimed is:
1. A compound selected from a group consisting of the following compounds:

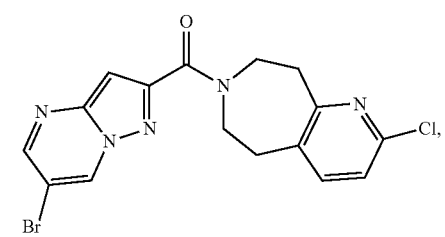

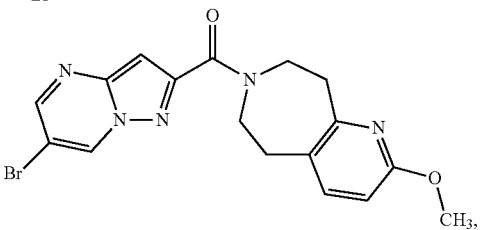

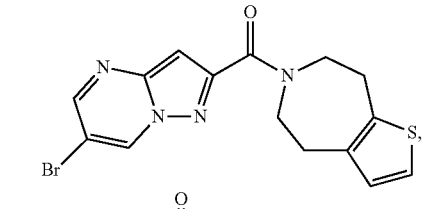

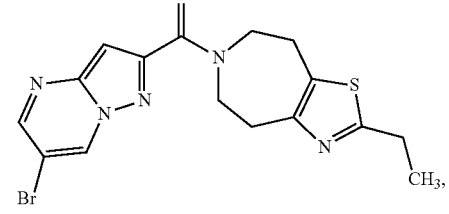

-continued

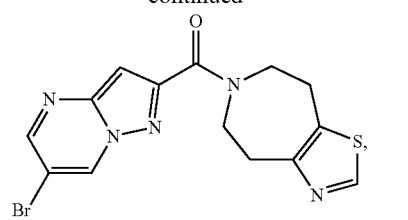

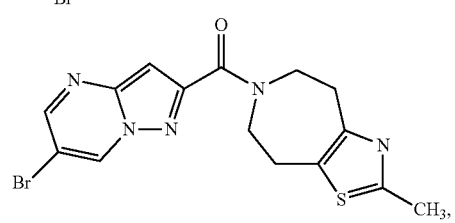

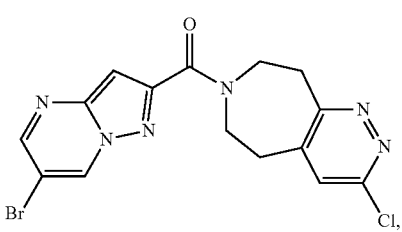

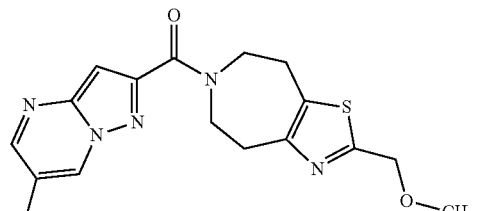

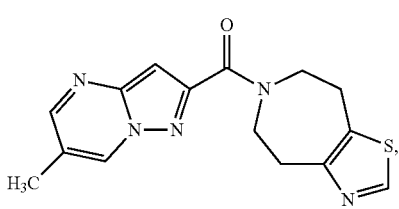

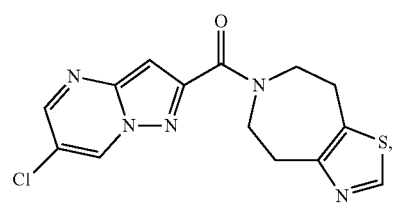

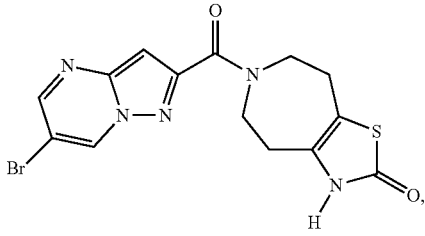

-continued

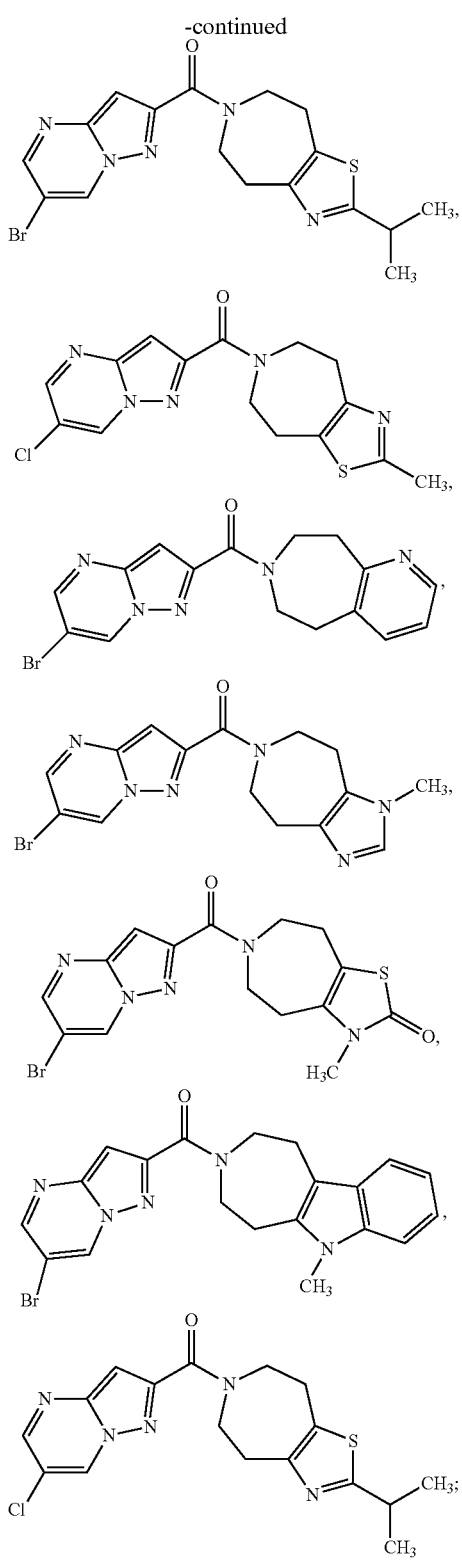

-continued

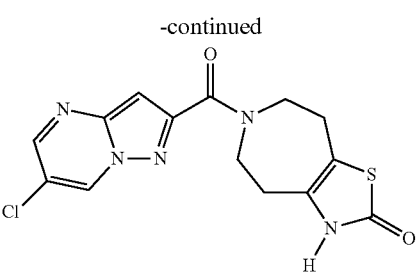

or a pharmaceutically acceptable salt thereof.

2. A pharmaceutical composition comprising at least one compound according to claim 1 or a pharmaceutically acceptable salt thereof in admixture with a pharmaceutically acceptable adjuvant, diluent and/or carrier.

3. A method of treating psychiatric diseases, disorders or conditions selected from a group consisting of psychotic disorders, schizophrenia, depression and bipolar mood disorders, anxiety disorders, general anxiety disorder, panic, post-traumatic stress, phobia, acute stress, paranoia, obsessive or compulsive disorders, anorexia, bulimia, personality disorders, failure to thrive, sexual dysfunction, substance related disorders and disorders of impulse control, comprising administering an effective amount of a compound according to claim 1 or a pharmaceutically acceptable salt thereof, to a patient in need.

4. A method of treating neurological diseases, disorders or conditions selected from a group consisting of epilepsy, Alzheimer's disease, cognitive disorders, memory deficits, Parkinson's disease, Aids related dementia, stroke, attention deficit/hyperactivity disorder, delirium tremens, neurodegeneration, neurotoxicity, Fragile X, amyotrophic lateral sclerosis, Huntington's Choria, autism, mental retardation, Down's syndrome and head trauma, comprising administering an effective amount of a compound according to claim 1 or a pharmaceutically acceptable salt thereof, to a patient in need.

5. A method of treating diseases, disorders or conditions selected from a group consisting of chronic migraine, acute migraine; neuralgia, post-herpetic neuralgia, trigeminal neuralgia, chemotherapy induced neuropathies, inflammatory pain, neuropathic pain, diabetic neuropathy, arthritis, rheumatoid diseases, low back pain, post-operative pain; pain associated with angina, menstruation, gout, renal colic and biliary colic, comprising administering an effective amount of a compound according to claim 1 or a pharmaceutically acceptable salt thereof, to a patient in need.

* * * * *